(12) United States Patent
Rizkalla et al.

(10) Patent No.: US 7,803,957 B2
(45) Date of Patent: Sep. 28, 2010

(54) ETHYLENE OXIDE PRODUCTION USING FIXED MODERATOR CONCENTRATION

(75) Inventors: Nabil Rizkalla, Rivervale, NJ (US); Howard Sachs, Bronx, NY (US); Mansoor Firoz Husain, North Brunswick, NJ (US); Christian J. Gueckel, Paramus, NJ (US); Andrzej Rokicki, Mountain Lakes, NJ (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 14 days.

(21) Appl. No.: 11/853,473

(22) Filed: Sep. 11, 2007

(65) Prior Publication Data

US 2009/0069583 A1 Mar. 12, 2009

(51) Int. Cl.
*C07D 301/10* (2006.01)
(52) U.S. Cl. ..................................... 549/536
(58) Field of Classification Search ................. 549/534, 549/536
See application file for complete search history.

(56) References Cited

U.S. PATENT DOCUMENTS

| | | | |
|---|---|---|---|
| 2,773,844 A | 12/1956 | Carlson et al. | |
| 3,423,328 A | 1/1969 | Keith et al. | |
| 3,563,913 A | 2/1971 | Krijger et al. | |
| 3,892,679 A | 7/1975 | Holler | |
| 4,066,575 A | 1/1978 | Winnick | |
| 5,703,253 A | 12/1997 | Evans et al. | |
| 5,719,299 A | 2/1998 | Te Raa | |
| 5,801,259 A | 9/1998 | Kowaleski | |
| 5,929,259 A | 7/1999 | Lockemeyer | |
| 6,372,925 B1 | 4/2002 | Evans et al. | |
| 6,717,001 B2 | 4/2004 | Evans et al. | |
| 2004/0014999 A1 * | 1/2004 | Chipman et al. | 549/534 |
| 2007/0142974 A1 | 6/2007 | Chipman et al. | |

FOREIGN PATENT DOCUMENTS

| | | | |
|---|---|---|---|
| EP | 057066 | * | 8/1982 |
| WO | WO 03-044002 | * | 5/2003 |

OTHER PUBLICATIONS

Montrasi, G. L., et al.; 1983. "Oxidation of Ethylene to Ethylene Oxide: Role of Organic Chlorides." Oxidation Communications 3, Nos. 3-4, 259-267.

* cited by examiner

*Primary Examiner*—Bernard Dentz
(74) *Attorney, Agent, or Firm*—Scully, Scott, Murphy & Presser, P.C.

(57) ABSTRACT

A method for controlling ethylene oxidation uses ethylene and oxygen, in conjunction with a silver based catalyst, a moderator and a co-moderator, to form ethylene oxide. When controlling the ethylene oxidation reaction, the moderator concentration is maintained constant within a comparatively narrow operative concentration range and the co-moderator concentration is varied within a comparatively wider operative concentration range, to optimize a catalyst property such as the catalyst activity and/or the catalyst selectivity.

16 Claims, No Drawings

ETHYLENE OXIDE PRODUCTION USING FIXED MODERATOR CONCENTRATION

BACKGROUND

1. Field of the Invention

The invention relates generally to process control within chemical reactions. More particularly, the invention relates to enhanced process control within ethylene oxidation chemical reactions.

2. Description of the Related Art

Commercially significant chemical reactions may in general be undertaken using either a batch processing chemical reactor or a continuous processing chemical reactor. Also included as adjunct materials to reactant materials and product materials within many commercially significant chemical reactions are: (1) catalyst materials that facilitate a chemical reaction of a particular reactant material to form a particular product material; (2) promoter materials that are typically incorporated into a particular catalyst material to promote performance of the particular catalyst material with respect to a particular chemical reaction (i.e., where such performance may be optimized with respect to at least a catalyst activity and a catalyst specificity); and (3) moderator materials that are intended to be incorporated within a particular reactant material batch or stream, and to appropriately moderate performance of a particular catalyst material with respect to a particular chemical reaction.

While there are many commercially significant chemical reactions that may be used to produce, in general, large quantities (i.e., thousands of tons per year) of organic chemical intermediate or product materials, inorganic chemical intermediate or product materials and hybrid organic and inorganic chemical intermediate or product materials, a particularly fundamental commercially significant chemical reaction is a chemical oxidation reaction (i.e., chemical epoxidation reaction) of ethylene with oxygen to form ethylene oxide (i.e., ethylene epoxide). In turn, the ethylene oxide that is formed from the foregoing chemical oxidation reaction may be hydrolyzed to form ethylene glycols which further comprise yet another commercially significant organic chemical product material and/or organic chemical intermediate material.

Commercially significant ethylene oxide production through the silver based catalyzed reaction of ethylene with molecular oxygen within a multi-tubular continuous reactor has been well known, productively used and incrementally improved for many decades. Notwithstanding the foregoing, due to the extraordinary volumes of scale within commercially significant ethylene oxide production, an otherwise seemingly inconsequential process improvement not yet implemented within commercially significant ethylene oxide production may nonetheless still yield a considerable economic dividend.

Various aspects of the ethylene oxide production through the silver based catalyzed reaction of ethylene and molecular oxygen are known in the chemical processing art. Of special interest is the application of a chloride moderator in this process. For instance R. McNamce, U.S. Pat. No. 2,238,474, disclosed the addition of ethylene dichloride to the ethylene oxidation feed to enhance the catalyst's efficiency.

G. Law, U.S. Pat. No. 2,279,469, disclosed that adding a halogen compound to the feed suppresses the formation of carbon dioxide.

G. Sears, U.S. Pat. No. 2,615,900, disclosed that addition of a metal halide to the silver catalyst reduced the formation of carbon dioxide.

D. Sacken, U.S. Pat. No. 2,765,283, disclosed that washing the carrier, which will be used to prepare ethylene oxide catalyst, with a chlorine containing compound resulted in higher conversion and higher yield Lauritzen, U.S. Pat. No. 4,874,879, disclosed the prechloriding of fresh Re-containing catalyst before adding oxygen to the feed.

M. Nakajima, U.S. Pat. No. 4,831,162, disclosed a feed that included a "chlorine-containing burning reaction de-accelerator" and an oxide of nitrogen for a highly selective catalyst containing Rb and silver.

T. Notermann, U.S. Pat. No. 4,994,587, and P. Hayden, U.S. Pat. No. 5,387,751, both disclosed a gas feed comprising a chloride moderator and an oxide of nitrogen for high selectivity catalyst.

P. Shankar, U.S. Pat. No. 5,155,242, disclosed that pre-chloriding the fresh catalyst will facilitate the start up of a catalyst containing Cs and silver. It was also disclosed that the pre-chloriding allows the start up of a Re containing catalyst at a lower temperature.

P. Hayden, EP 0057066, disclosed that chlorine containing moderators are of different effectiveness. If the feed contains several moderator compounds the catalyst's performance will be affected by the effective sum of the moderators and not their absolute sum.

Y. Oka, U.S. Pat. No. 6,300,507, disclosed the addition of the chloride moderator in the form of liquid that is injected in the feed steam.

W. Evans, U.S. Pat. Nos. 6,372,925 and 6,717,001, disclosed that for highly selective catalysts, the moderator's concentration has to be optimized repeatedly during the operation, in order to maintain maximum selectivity. Also it was disclosed that a small changes in the moderator's level exhibits pronounced effect on the catalytic performance.

Finally, P. Chipman, U.S. Pat. No. 7,193,094, disclosed that in operating a highly selective silver catalyst, the moderator level is adjusted with the change in reaction temperature.

Also in the open literature Montrasi et al., in "Oxidation of Ethylene to Ethylene Oxide: Role of Organic Chlorides," Oxidation Communications, Vol. 3 (3-4), 259-67 (1983), teaches an organic chloride moderator material that reversibly influences an activity and a selectivity of a silver based catalyst within a silver based catalyzed reaction of ethylene with molecular oxygen to form ethylene oxide. The moderator level has to be increased in response to a reduced catalyst activity. It was also taught within the foregoing reference that the use of a "chloride scavenger" material allows a wider operative range of the organic chloride moderator material.

Commercially significant chemical reactions, such as in particular ethylene oxidation reactions, are certain to continue to be prominent as domestic and world economies expand. Thus, desirable are methods whereby such commercially significant ethylene oxidation reactions may be efficiently optimized.

SUMMARY

The invention provides a method for optimizing a chemical reaction, and in particular an ethylene oxidation reaction. The method is applicable in particular for a catalyzed ethylene oxidation chemical reaction that uses a silver based catalyst that exhibits an aging effect. By "aging effect" it is meant that as a function of time of use of the silver based catalyst within the catalyzed ethylene oxidation chemical reaction at least one performance parameter of the silver based catalyst declines. The performance parameters may include, but is not necessarily limited to, a silver based catalyst activity and a silver based catalyst selectivity. The ethylene oxidation chemical reaction also uses a reactant gas mixture that includes a moderator that affects the performance of the silver based catalyst for the ethylene oxidation chemical reaction and a co-moderator that affects the silver based catalyst and the moderator for the ethylene oxidation chemical reaction. The invention does not intend that the co-moderator measurably affects (i.e., typically within the context of a silver based catalyst selectivity and/or a silver based catalyst activity) the silver based catalyst absent the moderator.

The invention provides particular value when an operative concentration range of the co-moderator is wider than an operative concentration range of the moderator. Under such circumstances, a concentration of the moderator that is effective in the narrower operative concentration range may be held constant while the concentration of the co-moderator that is operative in the wider operative concentration range may be varied to optimize (i.e., either continuously or discontinuously) the ethylene oxidation chemical reaction as the silver based catalyst that exhibits the aging effect ages. The invention provides value insofar as effectively controlling a concentration of the co-moderator that is effective in the wider operative concentration range generally provides a reduced impediment to effective chemical process control than controlling a concentration of the moderator that is effective in the narrower operative concentration range.

A particular method for controlling ethylene oxidation includes reacting ethylene with oxygen in the presence of a silver based catalyst, a moderator and a co-moderator, to form ethylene oxide. This particular method also includes holding constant the concentration of the moderator, but varying the concentration of the co-moderator as the silver based catalyst ages.

Another particular method for controlling ethylene oxidation includes reacting ethylene with oxygen in the presence of a silver based catalyst that includes a rhenium promoter, a moderator and a co-moderator, to form ethylene oxide. This other particular method also includes holding constant the concentration of the moderator, but varying the concentration of the co-moderator as the silver based catalyst ages.

Yet another particular method for controlling ethylene oxidation includes reacting ethylene and oxygen in the presence of a silver based catalyst, an organic halide moderator and an organic non-halide co-moderator, to form ethylene oxide. This other particular method also includes holding constant the concentration of the organic halide moderator, but varying the concentration of the organic non-halide co-moderator as the silver based catalyst ages.

The invention also provides an efficient method to maintain the catalyst's performance at its maximum value. It was discovered that when the performance of the catalyst is optimized via adjusting the moderator's concentration, the catalyst requires an extended period of time to adjust to the new level, 10-24 hours. By contrast, and unexpectedly, within the parameters of the instant invention, when the performance of the catalyst is optimized via adjusting the co-moderator's concentration, the catalyst requires a limited period of time to adjust to the new level, 4-8 hours

DESCRIPTION OF THE PREFERRED EMBODIMENT

The invention, which includes a method for optimizing an ethylene oxidation chemical reaction, is understood within the context of the description that follows. The particular embodiment within the following description is applicable under circumstances where an ethylene chemical reactant material is reacted to form an ethylene oxide chemical product material in the presence of a silver based catalyst, where the ethylene oxidation chemical reaction may be moderated to compensate for the aging effect by use of: (1) a moderator that is active with respect to the catalyst; and (2) a co-moderator that is active with respect to both the catalyst and the moderator.

Generally, a commercially practiced ethylene oxide production process provides for continuously contacting an oxygen containing oxidant gas with ethylene in the presence of a silver based catalyst within a reactor at a temperature in a range of from about 180° C. to about 330° C., more preferably from about 200° C. to about 325° C., and most preferably from about 210° C. to about 270° C. A reactor pressure may vary from about atmospheric pressure to about 30 atmospheres, depending on a mass velocity and productivity (i.e., production rate) desired. Higher reactor pressures may, however, be employed within the scope of any of several embodiments.

A feed gas mixture for an ethylene oxidation reaction may comprise about 0.5 to about 45% by volume ethylene, about 3 to 15% by volume oxygen, and up to about 8% by volume carbon dioxide. The oxygen level in the feed should not exceed the flammability level threshold, which will be mandated by the level of the hydrocarbons in the feed. A balance of the feed gas mixture may comprise comparatively inert materials including but not limited to nitrogen, methane, argon and the like. Typically, only a portion of an ethylene reactant gas and an oxygen oxidant gas is reacted per pass over a silver based catalyst within the reactor when reacting the ethylene reactant gas and the oxygen oxidant gas to form ethylene oxide. After separation of the desired ethylene oxide chemical reaction product, and the removal of undesirable inert gases and by-product gases, an unreacted ethylene reactant gas and unreacted oxygen oxidant gas are recycled to the reactor.

Within the context of the disclosure above, the instant embodiment is more particularly directed towards the use of both a moderator material (i.e., typically a gas) and a co-moderator material (i.e., typically also a gas) within a silver based catalyzed reaction of ethylene and oxygen to form ethylene oxide. Also pertinent to the instant embodiment is an interaction of the moderator material and co-moderator material with a silver based catalyst material. Thus, further discussion of the silver based catalyst material, the moderator material and the co-moderator material follows.

As noted within the context of disclosure above, a catalyst within an ethylene oxidation reaction is typically a silver based catalyst that is supported upon a ceramic support. Ceramic supports comprising alumina materials are particularly common. Other ceramic support materials, as either alternatives or additives, are not excluded, although they are generally less common. Suitable ceramic supports will typically have surface area from about 0.3 to about 2.0 square meters per gram, and a water absorption quantity from about 0.30 to about 0.60 milliliters per gram.

A ceramic support within a silver based catalyst includes a catalytically effective amount of silver located therein and/or thereupon. Such silver based catalysts are prepared by impregnating the ceramic support with at least one silver precursor material such as a silver ion, a silver compound, a silver complex or a silver salt, or alternatively a mixture thereof, dissolved in a suitable solvent appropriate to facilitate impregnation of the at least one silver precursor material within and upon the ceramic support. Such a silver precursor material impregnated ceramic support is then removed from the silver precursor material solution, and the at least one impregnated silver precursor material is transformed into a metallic silver material, typically but not exclusively by a high temperature calcination treatment. Also preferably deposited on the ceramic support either prior to, coincidentally with, or subsequent to, the impregnation of the at least one silver precursor material is at least one alkali metal promoter precursor material in the form of at least one alkali metal ion, compound or salt dissolved in a suitable solvent. Also preferably deposited on the ceramic support either prior to, coincidentally with, or subsequent to the impregnation of the at least one silver precursor material and/or the at least one alkali metal promoter precursor material, is at least one suitable transition metal promoter precursor material in the form of a transition metal promoter precursor ion, compound, complex and/or salt that is also dissolved in an appropriate solvent.

Generally, the ceramic support is impregnated with the silver precursor material impregnating solution, which is preferably an aqueous silver ion solution. The ceramic support may also be impregnated at the same time, or in a separate process step, with the alkali metal promoter precursor material and the transition metal promoter precursor material, as discussed above. Silver based catalysts prepared and used in accordance with the instant embodiment typically comprise up to about 45% by weight of silver, expressed as metal, deposited upon the surface and throughout the pores of a ceramic support. A silver content, expressed as metal, from about 1 to about 40% by weight of total catalyst is preferred, while a silver content of from about 8 to about 35% is more preferred. Particularly useful silver precursor materials non-exclusively include silver oxalate, silver nitrate, silver oxide, silver carbonate, silver carboxylate, silver citrate, silver phthalate, silver lactate, silver propionate, silver butyrate and higher fatty acid salts thereof and combinations thereof.

In accordance with disclosure above, an amount of silver deposited on a ceramic support or present on the ceramic support is an amount which is described as a "catalytically effective amount of silver" (i.e., an amount which economically catalyzes, for example, the reaction of ethylene and oxygen to produce ethylene oxide). As used within this disclosure, the term "catalytically effective amount of silver" is also intended to refer to an amount of silver that provides a measurable conversion of, for example, ethylene and oxygen to ethylene oxide with a stable activity and a stable selectivity during a catalyst life.

As described above, in addition to the catalytically effective amount of silver, a silver based catalyst in accordance with the embodiment also includes a promoting amount of an alkali metal promoter and a promoting amount of a transition metal promoter, each of which is also supported on the ceramic support. As used herein the term "promoting amount" of the alkali metal promoter or the transition metal promoter is intended to refer to an amount of that promoter component that works effectively to provide an improvement in one or more of the catalytic properties of the silver based catalyst when compared to a silver based catalyst not containing the particular promoter component. The exact concentration of a particular promoter will depend upon, among other factors, a desired silver content within a silver based catalyst, the nature of a carrier within a silver based catalyst, the viscosity of the impregnating solution and the solubility of a particular silver precursor material.

The silver precursor material and the promoter precursor material solution used to impregnate the ceramic support may also comprise an optional solvent or complexing/solubilizing agent such as is known in the art. A wide variety of solvents or complexing/solubilizing agents may be employed to solubilize a silver precursor material to a desired concentration in an impregnating solution. Useful complexing/solubilizing agents include amines, ammonia, or lactic acid. Amines include alkylene diamines, as well as alkanol amines having from 1 to 5 carbon atoms. In one embodiment, a particular impregnating solution comprises an aqueous solution of silver oxalate (i.e., as a silver precursor material) and ethylene diamine. In general, the complexing/solubilizing agent may be present in the impregnating solution in an amount of from about 0.1 to about 5.0 moles of ethylene diamine per mole of silver precursor material, preferably from about 0.2 to about 4.0 moles, and more preferably from about 0.3 to about 3.0 moles of ethylene diamine for each mole of silver precursor material. The concentration of a silver precursor material (i.e., such as a silver salt) in the impregnating solution is in a range from about 1% by weight to the maximum permitted by the solubility of the particular silver precursor material/solubilizing agent combination employed. It is generally suitable to employ silver precursor material solutions containing from about 7% to about 45% by weight of silver, with silver concentrations from about 10% to about 35% by weight being preferred.

Impregnation of a particular ceramic support is typically achieved in conventional manner by excess solution impregnation, incipient wetness, etc. Typically the ceramic support is immersed in the silver precursor material solution until a sufficient amount of the silver precursor material solution is absorbed into the ceramic support. Preferably the quantity of the silver precursor material solution used to impregnate the support is not more than is necessary to fill the pore volume of the support. The silver precursor material solution and/or promoter precursor material solution penetrates by absorption, capillary action and/or vacuum into the pores of the ceramic support. A single impregnation or a series of impregnations, with or without intermediate drying, may be used, depending in part on the concentration of the silver precursor material and/or promoter precursor materials in the impregnation solution. Known prior procedures of pre-deposition, co-deposition and post-deposition of various promoters can advantageously be employed to provide desirable catalytic properties of a silver based catalyst.

In particular, the standard catalyst that contains only silver and cesium, was prepared according to example 5 in U.S. Pat. No. 4,012,425. The highly selective catalyst that also contains Re as a promoter were prepared according to examples 5-10 of U.S. Pat. No. 4,766,105

Examples of catalytic properties of a silver based catalyst include, inter alia, operability (resistance to runaway), selectivity, activity, conversion, and stability. It is understood by one skilled in the art that one or more of the individual catalytic properties may be enhanced by the "promoting amount" of a promoter, while other catalytic properties may or may not be enhanced or may even be diminished. It is further understood that different catalytic properties may be enhanced at different operating conditions. For example, a catalyst having enhanced selectivity at one set of operating conditions for a chemical reaction that may be continuously optimized in accordance with the instant embodiment may be operated at a different set of conditions wherein an improvement is effected within the context of activity rather than the selectivity. In that regard, incident to operation of a chemical reactor system, such as an ethylene oxidation chemical reactor system, particular operating conditions may be changed in order to take advantage of certain catalytic properties even at the expense of other catalytic properties. Such optimized conditions and results may take into account feedstock costs, energy costs, by-product removal costs and the like.

After impregnation, the ceramic support impregnated with the silver precursor material and the promoter precursor material(s) is calcined for a time sufficient (or alternatively otherwise appropriately activated) to convert the silver precursor material to metallic silver and the promoter precursor materials to promoters, and to remove the solvent and volatile decomposition products from the resulting silver based catalyst. In particular, calcination is accomplished by heating the impregnated micro-porous carrier, preferably at a gradual rate, to a temperature in the range of from about 200° C. to about 600° C., preferably from about 220° C. to about 500° C., and more preferably from about 240° C. to about 450° C., at a reaction pressure in the range of from 0.5 to 35 bar, for a time sufficient to convert the impregnated silver precursor material to silver metal and promoter precursor materials to promoters, to decompose all or substantially all organic materials that are present and remove the same as volatiles. In general, higher calcination temperatures provide shorter calcination time periods. Calcination time periods from about 10 minutes to about 24 hours are common.

Within the instant embodiment, the moderator material typically includes, but is typically not limited to, organic chlorides such as but not limited to chloromethanes, chloroethanes, chloropropanes and other chloroalkanes, as well as chloroalkenes such as vinyl chlorides, and chloropropenes. Other organic chlorides, as well as other organic halides, are not excluded. In particular, the moderator material is intended to include the effective sum of all the organic chloride (or alternatively organic halide) moieties that are in a feed gas mixture. The quantity of the organic chloride moieties that is in the feed gas mixture is generally in the range of 0.5 to 50 parts per million, by volume. At the beginning of a silver based catalyst life cycle, the organic chloride concentration is generally in a range from about 0.5 to about 5 parts per million. Conventionally, this concentration is subsequently and frequently adjusted to higher concentrations as the silver based catalyst ages during the silver based catalyst life cycle. Precise control of the moderator material within a part per million concentration range within a continuous process is often difficult.

Within the instant embodiment, the co-moderator material typically includes, but is typically not limited to, an organic non-halide material, such as an organic non-chloride gas, such as but not limited to ethane, propane and/or butane, or alternative related alkanes. Such organic non-halide and non-chloride material co-moderators are typically present in a range from about 0.1 to about 10 percent by volume with respect to the sum of other feed gases within the feed gas mixture.

As is understood by a person skilled in the art, as a supported silver based catalyst ages the silver based catalyst loses activity. Thus, a higher reaction temperature will typically be required (in particular for a highly selective rhenium promoted supported silver based catalyst in comparison with a less selective supported silver based catalyst absent rhenium) to maintain an activity and a productivity of an aged silver based catalyst. With such an increase in the reaction temperature it will thus also be necessary to increase a moderator gas concentration to maintain a constant and optimum performance of the silver based catalyst.

The instant embodiment and the invention are predicated upon the consideration that it is more efficient to maintain a fixed moderator material concentration throughout a silver based catalyst life span. More particularly, within the context of the embodiment and the invention, this particular concentration will be equivalent to, or higher than, the highest concentration of the moderator material that is expected for a particular silver based catalyst.

For instance, the concentration of the effective sum of the chloro-hydrocarbon moderator materials for a fresh silver based catalyst that contains silver, and also cesium and rhenium as promoters, is typically in a range from about 0.5 to about 5 parts per million. The highest concentration of this moderator material throughout this supported silver based catalyst life could be about 5 to about 20 parts per million. In the instant embodiment, this higher concentration is used as a constant concentration throughout the silver based catalyst life. Within the instant embodiment, the use of a co-moderator material is provided as an adjunct component within a feed gas mixture. As the performance of a particular silver based catalyst declines with aging the instant embodiment provides for re-optimization of the level of the co-moderator material in order to retain optimum silver based catalyst performance.

In essence, according to the instant invention, at the beginning of a silver based catalyst life, a comparatively high concentration of an organic halide, such as an organic chloride, moderator material is sufficient to reduce the silver based catalyst activity to an undesirable level. The controlled addition of an organic non-halide co-moderator material, however, is capable of restoring optimal performance to the silver based catalyst. At this stage in the life-span of the silver based catalyst, the concentrations of both the moderator material and the co-moderator material are at their maximum values. Within the context of the embodiment and the invention, as the silver based catalyst ages, the moderator material concentration in the feed gas mixture is not changed, but the co-moderator material concentration is gradually adjusted to maintain and secure optimum performance for the silver based catalyst.

As disclosed above, the co-moderator material is preferably an organic non-halide (i.e., non-chloride) material, such as but not limited to ethane or propane. When an appropriate concentration of the co-moderator material is included in the feed gas mixture, the silver based catalyst gains a higher activity and/or a higher selectivity. As the silver based catalyst ages its performance declines and it will be necessary to gradually reduce the concentration of the co-moderator material. This controlled reduction of the concentration of the co-moderator material is intended to restore the optimal performance of the silver based catalyst, in particular with respect to the silver based catalyst activity when the silver based catalyst is a highly selective silver based catalyst.

For reference purposes, a "selectivity" of a silver based catalyst is intended as a proportion of a reactant (i.e., ethylene) which is converted to a product in a particular chemical reaction.

$$\text{Selectivity (\%)} = \frac{\text{Moles of ethylene converted to ethylene oxide}}{\text{Moles of reacted ethylene}} \times 100$$

In accordance with the embodiment and the invention, an operative concentration range for the co-moderator material is generally greater than an operative concentration range of the moderator material. This greater operative concentration range for the co-moderator material is generally easily controlled and its magnitude generally also allows for minor variation. For instance, in the instant embodiment a fresh silver based catalyst may have a peak performance with an organic halide (i.e., chloride) moderator material gas concentration in a range from about 0.5 to about 5 ppm and an alkane organic non-halide (i.e., non-chloride) co-moderator material in a concentration range from about 0.1 to about 5% of the feed gas mixture. In accordance with the instant embodiment, at the end of the silver based catalyst life, the organic halide moderator gas concentration is unchanged, but the organic non-halide co-moderator gas concentration may typically be in a concentration range from about 0.01 to about 1.0%.

As a more specific embodiment of the invention, at the startup of an ethylene oxidation reaction with fresh silver based catalyst, an organic halide moderator gas is added to the feed gas mixture at a temperature that is lower than the normal operating temperature (i.e., 120-200° C.). At this comparatively low temperature, the fresh silver based catalyst will show no activity, or a reduced activity, depending on the feed gas mixture composition. From the start, the concentration of the moderator material in the feed gas mixture is adjusted to the constant level that will be utilized throughout the silver based catalyst life. Simultaneously, the feed gas mixture is selected to include a maximum level of the co-moderator material. As the silver based catalyst ages, the performance of the silver based catalyst is optimized by continuously adjusting the concentration of the co-moderator material.

In another particular more specific embodiment, at the startup of a fresh silver based catalyst, the organic halide moderator gas is also added to the feed gas mixture at a temperature that is lower than the normal operating temperature (i.e., 120-200° C.). At this comparatively lower temperature the silver based catalyst will show a reduced activity, depending on a particular feed gas mixture. From the start of a particular chemical reaction, the concentration of the moderator material in the feed gas mixture is adjusted to the constant level that will be utilized throughout the silver based catalyst life.

At this initial stage of the particular chemical reaction, no co-moderator material is necessarily added. Rather, the co-moderator material will be added when it is apparent that the moderator material concentration provides a constant influence upon the silver based catalyst. The particular composition of an effluent gas may be used to define when this particular condition is attained, and at this point the co-moderator material will be added to the feed gas mixture. Alternatively, the silver based catalyst activity (i.e., productivity) may be used to define if the supported silver based catalyst surface and the moderator material in the feed gas mixture have reached equilibrium. During this initial phase of the silver based catalyst life, and with the increased concentration of the moderator material in use, the silver based catalyst will typically have a substantially reduced activity.

As the co-moderator material is added, the silver based catalyst activity increases, and, for example, an expected olefin oxidation reaction efficiently initiates. At this point a concentration of the co-moderator material in the feed gas mixture should be increased to achieve optimum performance of the silver based catalyst, for both selectivity and activity. The particular optimum performance should be evident when a further increase in the co-moderator material concentration results in the drop of the silver based catalyst selectivity. This optimum level of the co-moderator material will be the highest level that is expected to be used to continuously control the silver based catalyst activity.

Throughout the life of the silver based catalyst, the performance of the catalyst drops and higher reaction temperature will typically be required to maintain the productivity of the silver based catalyst. With such an increase in a reaction temperature it will typically be necessary to adjust the co-moderator material to regain the optimum performance of the supported silver based catalyst. As the catalyst continues to age and after several reductions of the co-moderator material concentration, a subsequent optimum performance will be lower than initial optimum performance at the beginning of the silver based catalyst life. Lower catalyst activity and/or lower catalyst selectivity will result. At the end of the silver based catalyst life, a concentration of the co-moderator material will be particularly low and the catalyst performance will decline to a level that requires replacement of the catalyst, as determined by economic considerations.

EXAMPLES

Examples 1-3

Silver based catalyst preparation and activation followed generally conventional procedures, as disclosed above. A 150 g portion of alumina support A was placed in a flask and evacuated to ca. 0.1 torr prior to impregnation. To the above silver solution were added aqueous solutions of cesium hydroxide, perrhenic acid, and ammonium sulfate in order to prepare a catalyst composition according to examples 5-10 of U.S. Pat. No. 4,766,105. Calcination of the wet catalyst was done on a moving belt calciner. In this unit, the wet catalyst is transported on a stainless steel belt through a multi-zone furnace. All zones of the furnace are continuously purged with pre-heated, ultra-high purity nitrogen and the temperature is increased gradually as the catalyst passes from one zone to the next. The heat is radiated from the furnace walls and from the preheated nitrogen.

In this Example 1, the wet catalyst entered the furnace at ambient temperature. The temperature was then increased gradually to a maximum of about 450° C. as the catalyst passed through the heated zones. In the last (cooling) zone, the temperature of the now activated catalyst was immediately lowered to less than 100° C. before it emerged into ambient atmosphere. The total residence time in the furnace was approximately 45 minutes.

The silver based catalyst was charged into a 32.5 mm reactor tube and was tested with a feed gas mixture that included the following components:

25% ethylene;

7% oxygen;

1% carbon dioxide;

3 parts per million, ethyl chloride (moderator); and 0.25% ethane (co-moderator).

The flow rate of the feed gas mixture was adjusted to provide a gas space velocity of 3200 hr$^{-1}$, and the temperature of the reactor was optimized to give productivity (work rate) of 220 Kg ethylene oxide per cubic meter of silver based catalyst per hour. The feed gas mixture was modified, to obtain optimum selectivity, by changing the concentration of either the moderator material or the co-moderator material. Resulting measured operating parameters are reported in Table 1.

TABLE 1

| Example | Optimization | Moderator ppm | Co-moderator % | Time required* | Selectivity | Reaction temperature |
|---|---|---|---|---|---|---|
| 1 | Initial composition | 3 | 0.25 | | 86% | 227 |
| 2 | Standard optimization (comparative) | 2.8 | 0.25 | 22 hours | 88.5 | 230 |
| 3 | According to this disclosure | 3 | 0.5 | 8 hours | 89.0 | 229.5 |

*The time required to achieve a steady state performance.

The tabular results illustrate that optimum conditions can be achieved in a shorter time when the co-moderator material concentration is varied.

Examples 4-5

The same silver based catalyst and the same procedure that was used in examples 1-3 was repeated with an exception that an aim of modifying the feed gas mixture composition was to optimize the reaction temperature. Results are illustrated in Table 2.

TABLE 2

| Example | Optimization | Moderator ppm | Co-moderator % | Time required* | Selectivity | Reaction temperature |
|---|---|---|---|---|---|---|
| 4 | Initial composition | 4 | 2.2 | | 89.2% | 232 |
| 5 | According to this disclosure | 4 | 1.85 | 7 hours | 89.0 | 229 |

Examples 4 and 5 illustrate that at a constant moderator concentration, a lowered co-moderator concentration may yield a more efficient reaction at lower temperature with a minimal compromise in selectivity.

Example 6

The same silver based catalyst that was used in previous examples was again used. Within this example, the co-moderator material concentration was continuously reduced over time to maintain optimal performance of a silver based catalyst, while the moderator material concentration was constant. Results are illustrated in Table 3.

TABLE 3

| Optimization # | Time, hr | Moderator, ppm | Co-moderator, % | Sel, mol % | Temp, ° C. |
|---|---|---|---|---|---|
| Initial | 100 | 10 | 1.74 | 90.2 | 229 |
| | 120 | 10 | 1.74 | 90.3 | 231 |
| 1 | 120 | 10 | 1.64 | 90.3 | 231 |
| | 970 | 10 | 1.64 | 90.2 | 229 |
| 2 | 1450 | 10 | 1.59 | 90.2 | 229 |
| 3 | 1650 | 10 | 1.56 | 90.2 | 229.5 |
| 4 | 1850 | 10 | 1.51 | 90.3 | 229 |
| 5 | 2020 | 10 | 1.51 | 90.1 | 230 |
| 6 | 2220 | 10 | 1.49 | 90.2 | 230 |
| 7 | 2400 | 10 | 1.49 | 90.1 | 229 |

The results of Table 3 clearly illustrate that a moderator material concentration within an ethylene oxidation reaction may be held constant, and a co-moderator material concentration may be lowered as a silver based catalyst within the ethylene oxidation reaction ages, to maintain performance of the silver based catalyst within the ethylene oxidation reaction.

The preferred embodiment and examples of the invention are illustrative of the invention rather than limiting of the invention. Revisions and modifications may be made to methods, materials, apparatus and dimensions in accordance with the preferred embodiment and examples of the invention while still providing embodiments and examples in accordance with the invention, further in accordance with the accompanying claims.

What is claimed is:

1. A method for controlling ethylene oxidation comprising:
reacting a feed gas mixture comprised of ethylene, oxygen, a moderator, and a co-moderator with a silver-based catalyst comprising at least rhenium in a promoting amount to form ethylene oxide; and
holding constant the concentration of the moderator, while progressively reducing the concentration of said co-moderator through the usable life of the silver-based catalyst such that the reaction temperature is maintained through the usable life of the silver-based catalyst.

2. The method of claim 1 wherein, through the usable life of the silver-based catalyst, aging of the silver-based catalyst is evident in a progressively diminished catalyst activity.

3. The method of claim 1 wherein, through the usable life of the silver-based catalyst, aging of the silver-based catalyst is evident in a progressively diminished catalyst selectivity.

4. The method of claim 1 wherein the silver-based catalyst comprises a supported silver-based catalyst.

5. The method of claim 1 wherein:
the moderator is active in a first concentration range with respect to the silver-based catalyst; and
the co-moderator is active in a second concentration range greater than the first concentration range with respect to both the silver-based catalyst and the moderator.

6. The method of claim 1 wherein the moderator comprises an organic halide.

7. The method of claim 1 wherein the co-moderator comprises an organic non-halide.

8. The method of claim 7 wherein said organic non-halide is one of ethane, propane and butane.

9. The method of claim 8 wherein said organic non-halide is ethane.

10. A method for controlling ethylene oxidation comprising:
reacting a feed gas mixture comprised of ethylene, oxygen, an organic halide moderator, and an organic non-halide co-moderator with a silver-based catalyst comprising at least rhenium in a promoting amount to form ethylene oxide; and
holding constant the concentration of the organic halide moderator, while progressively reducing the concentration of said non-halide co-moderator through the usable life of the silver-based catalyst such that the reaction temperature is maintained through the usable life of the silver-based catalyst.

11. The method of claim 10 wherein:
the organic halide moderator is active in a first concentration range with respect to the silver-based catalyst; and
the organic non-halide co-moderator is active in a second concentration range greater than the first concentration range with respect to both the silver-based catalyst and the organic halide moderator.

12. The method of claim 10 wherein said organic non-halide is one of ethane, propane and butane.

13. The method of claim 1 wherein the concentration of said co-moderator is varied within a concentration range of about 0.1 to about 10% by volume of the feed gas mixture.

14. The method of claim 1 wherein the concentration of said co-moderator is varied within a concentration range of about 0.1 to about 5% by volume of the feed gas mixture.

15. The method of claim 1, wherein, at an initial steady state period of catalyst operation, the co-moderator has a concentration within a concentration range of about 0.1% to about 5% by volume of the feed gas mixture, while at the end of the usable life of the catalyst, the co-moderator has a concentration within a concentration range of about 0.01% to about 1% by volume of the feed gas mixture.

16. The method of claim 10, wherein, at an initial steady state period of catalyst operation, the co-moderator has a concentration within a concentration range of about 0.1% to about 5% by volume of the feed gas mixture, while at the end of the usable life of the catalyst, the co-moderator has a concentration within a concentration range of about 0.01% to about 1% by volume of the feed gas mixture.

* * * * *